(12) United States Patent
Kim et al.

(10) Patent No.: US 9,986,977 B2
(45) Date of Patent: Jun. 5, 2018

(54) ULTRASONIC DIAGNOSTIC APPARATUS AND METHOD OF OPERATING THE SAME

(71) Applicant: SAMSUNG MEDISON CO., LTD., Gangwon-Do (KR)

(72) Inventors: Nam-Woong Kim, Gangwon-do (KR); Gil-Ju Jin, Gangwon-do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 695 days.

(21) Appl. No.: 14/493,112

(22) Filed: Sep. 22, 2014

(65) Prior Publication Data
US 2015/0265253 A1    Sep. 24, 2015

(30) Foreign Application Priority Data

Mar. 18, 2014   (KR) .................. 10-2014-0031820

(51) Int. Cl.
*A61B 8/00*  (2006.01)

(52) U.S. Cl.
CPC .............. *A61B 8/54* (2013.01); *A61B 8/4281* (2013.01); *A61B 8/4477* (2013.01); *A61B 8/4405* (2013.01); *A61B 8/4444* (2013.01); *A61B 8/585* (2013.01)

(58) Field of Classification Search
CPC ....... A61B 8/54; A61B 8/4477; A61B 8/4281; A61B 8/585; A61B 8/4405; A61B 8/4444
See application file for complete search history.

(56) References Cited

U.S. PATENT DOCUMENTS

| | | | | |
|---|---|---|---|---|
| 5,505,203 A | * | 4/1996 | Deitrich | A61B 8/00 600/437 |
| 5,552,645 A | * | 9/1996 | Weng | A61B 5/0002 307/112 |
| 5,776,065 A | * | 7/1998 | Mehmanpazir | A61B 8/00 600/437 |
| 6,261,249 B1 | | 7/2001 | Talish et al. | |
| 6,409,665 B1 | | 6/2002 | Scott et al. | |
| 8,403,853 B2 | | 3/2013 | Nakamura | |

(Continued)

FOREIGN PATENT DOCUMENTS

| | | |
|---|---|---|
| JP | 2011-067544 A | 4/2011 |
| KR | 2006-0075733 A | 7/2006 |

(Continued)

OTHER PUBLICATIONS

International Search Report and Written Opinion issued in counterpart International Patent Application dated Dec. 30, 2014; 12 pages in English language.

*Primary Examiner* — Long V Le
*Assistant Examiner* — Angela M Hoffa
(74) *Attorney, Agent, or Firm* — McDermott Will & Emery LLP (57) ABSTRACT

Provided are an ultrasonic diagnostic apparatus and a method of operating the same. The ultrasonic diagnostic apparatus includes: a first ultrasonic transceiver that transmits an ultrasonic signal and receives a first echo signal that is reflected, through a deactivated probe from among a plurality of probes; a gel detector that determines whether gel is applied on the deactivated probe based on the received first echo signal; and a controller that activates the deactivated probe when it is determined that the gel is applied on the deactivated probe.

15 Claims, 7 Drawing Sheets

(56) References Cited

U.S. PATENT DOCUMENTS

| | | | |
|---|---|---|---|
| 9,504,446 B2 * | 11/2016 | Jaeger | A61N 7/02 |
| 9,610,065 B2 * | 4/2017 | Kim | A61B 8/54 |
| 2005/0113699 A1 | 5/2005 | Haugen et al. | |
| 2006/0173346 A1 | 8/2006 | Lee | |
| 2006/0241464 A1 | 10/2006 | Ohtake et al. | |
| 2007/0232907 A1 * | 10/2007 | Pelissier | A61B 8/00 600/437 |
| 2013/0072800 A1 | 3/2013 | Lee | |
| 2014/0107487 A1 * | 4/2014 | Kim | A61B 8/4263 600/459 |
| 2015/0045673 A1 * | 2/2015 | Kim | A61B 8/4438 600/459 |
| 2016/0106396 A1 * | 4/2016 | Jin | A61B 8/54 600/437 |
| 2016/0183920 A1 * | 6/2016 | Woo | A61B 8/54 600/440 |

FOREIGN PATENT DOCUMENTS

| | | |
|---|---|---|
| KR | 2007-0022291 A | 2/2007 |
| KR | 10-2011-0083781 A | 7/2011 |
| KR | 10-2013-0030664 A | 3/2013 |
| KR | 10-1263831 | 5/2013 |

\* cited by examiner

ULTRASONIC DIAGNOSTIC APPARATUS AND METHOD OF OPERATING THE SAME

RELATED APPLICATIONS

This application claims the benefit of Korean Patent Application No. 10-2014-0031820, filed on Mar. 18, 2014, in the Korean Intellectual Property Office, the disclosure of which is incorporated herein in its entirety by reference.

BACKGROUND

1. Field

One or more embodiments of the present invention relate to an ultrasonic diagnostic apparatus and a method of operating the same, and more particularly, to an ultrasonic diagnostic apparatus capable of automatically changing a probe, and a method of operating the same.

2. Description of the Related Art

An ultrasonic diagnostic apparatus irradiates an ultrasonic signal generated by a transducer of a probe to a target object, and receives information about an echo signal reflected from the target object to obtain an image of a region inside the target object. In detail, the ultrasonic diagnostic apparatus is used for medical purposes, for example, to observe the inside of the target object, to detect a foreign substance, and to measure an injury. Such an ultrasonic diagnostic apparatus is widely used together with another imaging diagnostic apparatus since the ultrasonic diagnostic apparatus has high stability compared to a diagnostic apparatus using an X-ray, is capable of displaying an image in real-time, and is safe because of no radiation exposure.

Meanwhile, the ultrasonic diagnostic apparatus may provide a brightness (B) mode that displays reflection coefficients of an ultrasonic signal reflected from a target object in a 2-dimensional (2D) image, a Doppler mode that displays an image of a moving target object, in detail, a blood flow, by using a Doppler effect, an elastic mode that displays an image showing a difference between a reaction when compression is applied to a target object and a reaction when compression is not applied.

SUMMARY

One or more embodiments of the present invention include an ultrasonic diagnostic apparatus that is capable of automatically changing a probe by determining a will of a user to change the probe, for example, an act of applying gel to the probe, and a method of operating the ultrasonic diagnostic apparatus.

Additional aspects will be set forth in part in the description which follows and, in part, will be apparent from the description, or may be learned by practice of the presented embodiments.

According to one or more embodiments of the present invention, an ultrasonic diagnostic apparatus includes: a first ultrasonic transceiver that transmits an ultrasonic signal and receives a first echo signal that is reflected, through a deactivated probe from among a plurality of probes; a gel detector that determines whether gel is applied on the deactivated probe based on the first echo signal; and a controller that activates the deactivated probe when it is determined that the gel is applied on the deactivated probe.

The controller may obtain information about the deactivated probe, and the first ultrasonic transceiver, based on the obtained information, may determine a transmission frequency of the ultrasonic signal and a reception bandwidth of the first echo signal, transmit the ultrasonic signal according to the determined transmission frequency, and receive the first echo signal according to the determined reception bandwidth.

The deactivated probe may include at least one element, and the first ultrasonic transceiver may transmit the ultrasonic signal and receive the first echo signal through the at least one element.

The deactivated probe may include a first element and a second element, and the first ultrasonic transceiver may operate in at least one of a first mode for transmitting the ultrasonic signal and receiving the first echo signal through the first element, a second mode for transmitting the ultrasonic signal and receiving the first echo signal through the second element, a third mode for transmitting the ultrasonic signal through the first element and receiving the first echo signal through the second element, and a fourth mode for transmitting the ultrasonic signal through the second element and receiving the first echo signal through the first element.

The first ultrasonic transceiver, based on information about a probe among the plurality of probes, may transmit an ultrasonic signal to the probe on which gel is applied, and receive a second echo signal, the controller may set a gel detection threshold value based on the second echo signal, and the gel detector may determine whether the gel is applied on the deactivated probe by comparing a value of the first echo signal and the gel detection threshold value.

The gel detector may determine that the gel is applied on the deactivated probe when the value of the first echo signal is higher than the gel detection threshold value.

The ultrasonic diagnostic apparatus may further include: a beam former that performs beamforming by receiving an ultrasonic signal from an activated probe from among the plurality of probes; and a probe selector that deactivates at least one probe from among the plurality of probes by electrically disconnecting the at least one probe from the beam former, or activates the at least one probe by electrically connecting the at least one probe to the beam former.

The ultrasonic diagnostic apparatus may further include: a second ultrasonic transceiver that transmits an ultrasonic signal to an activated probe from among the plurality of probes, and receives a third echo signal that is reflected; and an image generator that generates an ultrasonic image based on the third echo signal.

According to one or more embodiments of the present invention, a method of operating an ultrasonic diagnostic apparatus, the method includes: transmitting an ultrasonic signal and receiving a first echo signal that is reflected, through a deactivated probe from among a plurality of probes; determining whether gel is applied on the deactivated probe based on the received first echo signal; and activating the deactivated probe when it is determined that the gel is applied on the probe.

The method may further include obtaining information about the deactivated probe, wherein the transmitting of the ultrasonic signal and receiving of the first echo signal may include, based on the obtained information, determining a transmission frequency of the ultrasonic signal and a reception bandwidth of the first echo signal, transmitting the ultrasonic signal according to the determined transmission frequency, and receiving the first echo signal according to the determined reception bandwidth.

The deactivated probe may include at least one element, and the transmitting of the ultrasonic signal and receiving of the first echo signal may include transmitting the ultrasonic signal and receiving the first echo signal through the at least one element.

The deactivated probe may include a first element and a second element, and the transmitting of the ultrasonic signal and receiving of the first echo signal may include at least one of operating in a first mode for transmitting the ultrasonic signal and receiving the first echo signal through the first element, operating in a second mode for transmitting the ultrasonic signal and receiving the first echo signal through the second element, operating in a third mode for transmitting the ultrasonic signal through the first element and receiving the first echo signal through the second element, and operating in a fourth mode for transmitting the ultrasonic signal through the second element and receiving the first echo signal through the first element.

The method may further include: based on information about a probe among the plurality of probes, transmitting an ultrasonic signal to the probe on which gel is applied, and receiving a second echo signal; and based on the second echo signal, setting a gel detection threshold value, wherein the determining of whether the gel is applied on the deactivated probe may include determining whether the gal is applied on the deactivated probe by comparing a value of the first echo signal and the gel detection threshold value.

The determining of whether the gel is applied on the deactivated probe may include determining that the gel is applied on the deactivated probe when the value of the first echo signal is higher than the gel detection threshold value.

The method may further include: deactivating at least one probe from among the plurality of probes by electrically disconnecting the at least one probe from a beam former or activating the at least one probe by electrically connecting the at least one probe to the beam former; and performing beamforming by receiving an ultrasonic signal from an activated probe from among the plurality of probes.

The method may further include: transmitting an ultrasonic signal to an activated probe from among the plurality of probes, and receiving a third echo signal that is reflected; and generating an ultrasonic image based on the third echo signal.

BRIEF DESCRIPTION OF THE DRAWINGS

These and/or other aspects will become apparent and more readily appreciated from the following description of the embodiments, taken in conjunction with the accompanying drawings in which:

FIGS. 7 (a), 7 (b), 7 (c) and 7 (d) illustrate reference diagrams for describing the method of FIG. 6.

DETAILED DESCRIPTION

The terms used in this specification are those general terms currently widely used in the art in consideration of functions in regard to the present invention, but the terms may vary according to the intention of those of ordinary skill in the art, precedents, or new technology in the art. Also, specified terms may be selected by the applicant, and in this case, the detailed meaning thereof will be described in the detailed description of the invention. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

Throughout the specification, an "ultrasonic image" refers to an image of a target object obtained using an ultrasonic wave. Furthermore, in the present specification, a "target object" may include a person or an animal, or a part of a person or an animal. For example, the target object may include the liver, the heart, the womb, the brain, a breast, the abdomen, or a blood vessel. Furthermore, the "target object" may include a phantom. A phantom is a material having a volume that is approximately the density and effective atomic number of a living thing, and may include a sphere phantom having a property similar to a human body.

An ultrasonic image may be variously realized. For example, an ultrasonic image may be at least one of an amplitude (A) mode image, a brightness (B) mode image, a color (C) mode image, and a Doppler (D) mode image. Alternatively, according to an embodiment of the present invention, an ultrasonic image may be a 2-dimensional (2D) image or a 3D image.

Furthermore, in the present specification, "user" refers to a medical professional, such as a doctor, a nurse, a medical laboratory technologist, or an engineer who repairs a medical apparatus, but the user is not limited thereto.

Expressions such as "at least one of," when preceding a list of elements, modify the entire list of elements and do not modify the individual elements of the list.

Embodiments of the invention now will be described more fully hereinafter with reference to the accompanying drawings, in which illustrative embodiments of the invention are shown.

Figure 1:
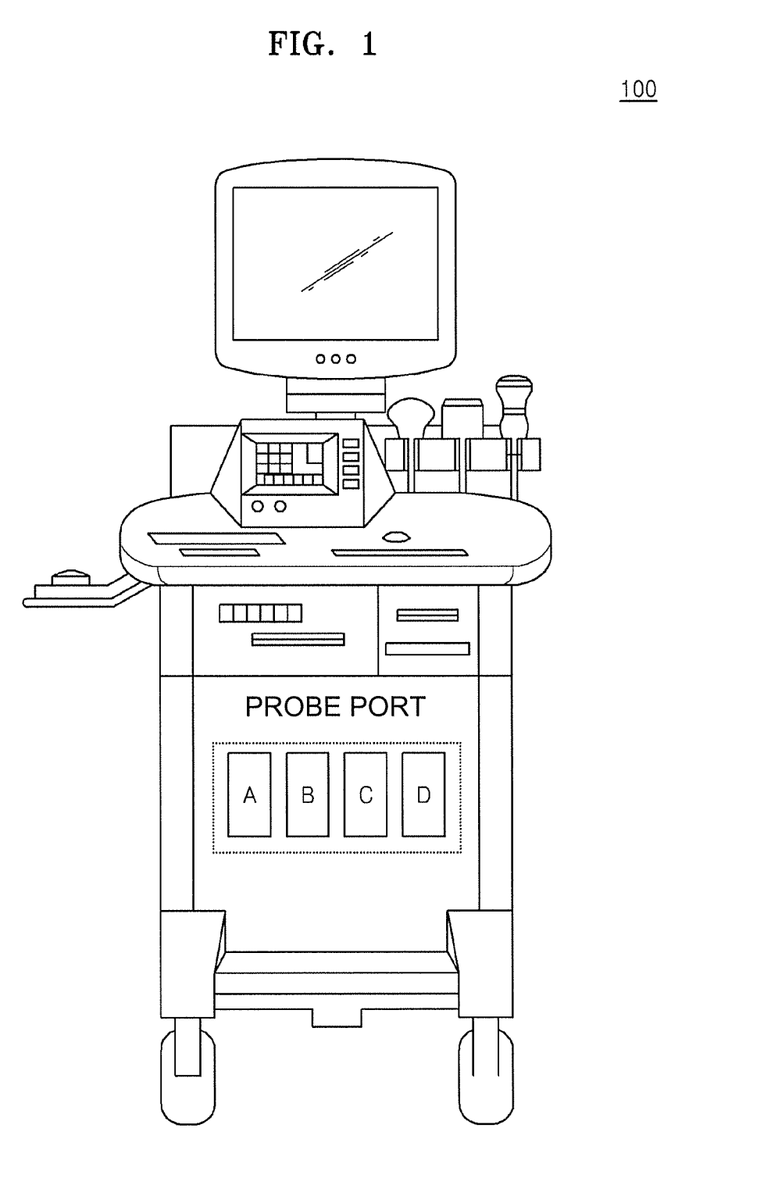
FIG. 1 is a diagram of an exterior of an ultrasonic diagnostic apparatus, according to an embodiment of the present invention.

FIG. 1 is a diagram of an exterior of an ultrasonic diagnostic apparatus 100, according to an embodiment of the present invention.

Referring to FIG. 1, the ultrasonic diagnostic apparatus 100 may include a plurality of probe ports A through D, and a plurality of probes may be connected to a main body of the ultrasonic diagnostic apparatus 100 via the probe ports A through D.

Accordingly, a user may respectively pre-connect the plurality of probes to the plurality of probe ports according to purpose, and may select and use at least one of the pre-connected probes according to diagnostic situations.

Here, the ultrasonic diagnostic apparatus 100 may automatically select a probe by determining whether gel is applied to a probe connected to a probe port. Also, the ultrasonic diagnostic apparatus 100 may activate the selected probe, transmit an ultrasonic signal to the activated probe, receive a reflected echo signal, and obtain an ultrasonic image.

Meanwhile, the ultrasonic diagnostic apparatus 100 according to an embodiment of the present invention may be embodied not only as a cart type apparatus, but also as a portable apparatus. Examples of portable ultrasonic diagnostic apparatuses may include a picture archiving and communications system (PACS) viewer, a smart phone, a laptop computer, a personal digital assistant (PDA), and a tablet PC, but are not limited thereto.

Figure 2:
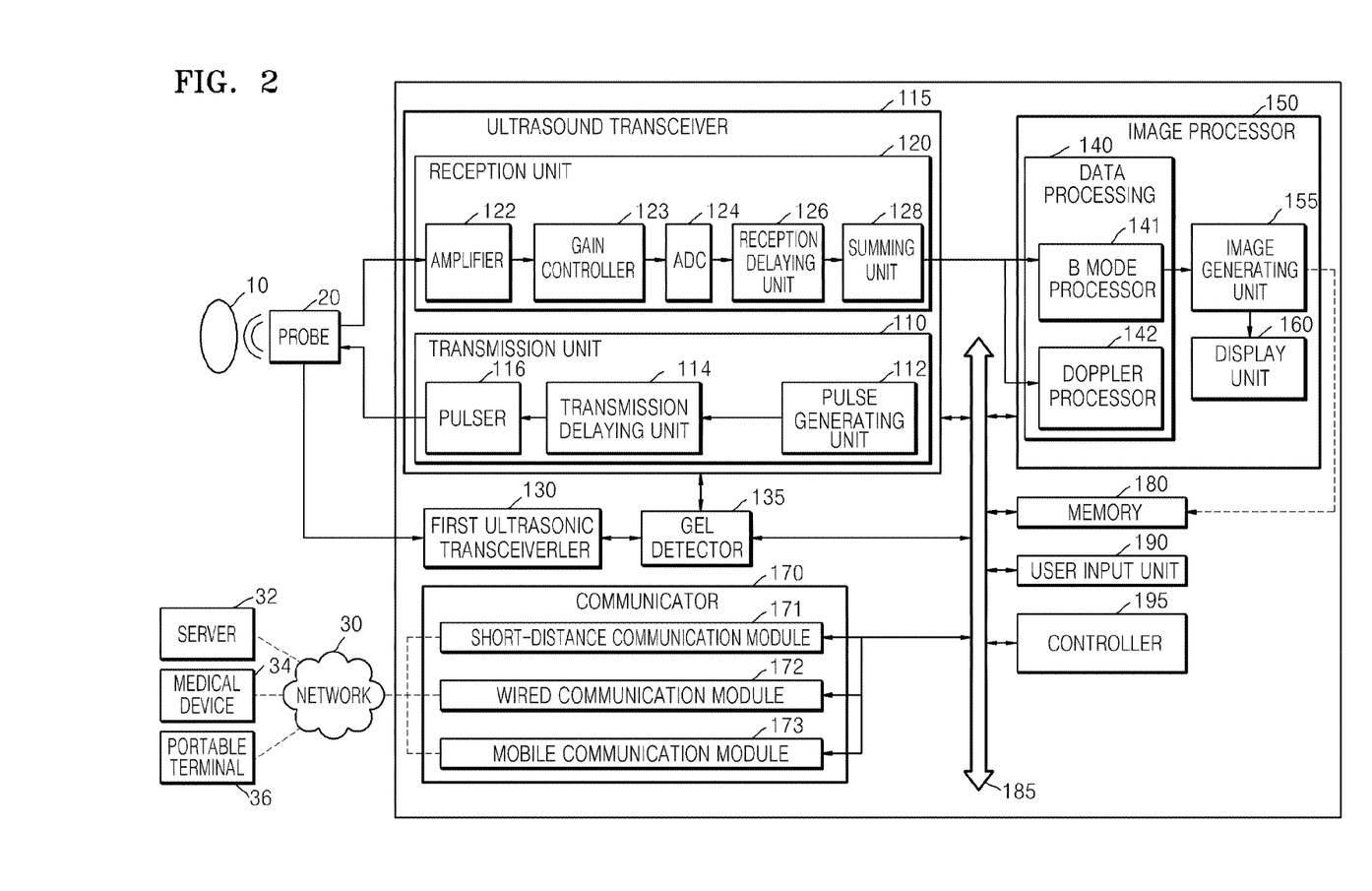
FIG. 2 is a block diagram of an ultrasonic diagnostic apparatus according to an embodiment of the present invention.

FIG. 2 is a block diagram of the ultrasonic diagnostic apparatus 100 according to an embodiment of the present invention.

Referring to FIG. 2, the ultrasonic diagnostic apparatus 100 may include a probe 20, a first ultrasonic transceiver 130, a second ultrasonic transceiver 115, a gel detector 135, an image processor 150, a communication unit 170, a memory 180, a user input unit 190, and a controller 195, which may be connected to each other via a bus 185.

The probe 20 transmits an ultrasonic signal to a target object 10 based on a driving signal applied by the first and second ultrasonic transceivers 130 and 115 and receives an echo signal reflected by the target object 10. The probe 20 includes a plurality of transducer elements and the plurality of transducer elements oscillate based on electric signals transmitted thereto and generate acoustic energy, that is, ultrasonic waves. Furthermore, the probe 20 may be connected to a main body of the ultrasonic diagnostic apparatus 100 via wires or wirelessly. According to embodiments of the present invention, the ultrasonic diagnostic apparatus 100 may include a plurality of probes 20.

The first and second ultrasonic transceivers 130 and 115 transmit an ultrasonic signal and receive an echo signal that is reflected, through the probe 20.

Here, the first ultrasonic transceiver 130 may transmit and receive ultrasonic waves to detect whether gel is applied on a probe. The first ultrasonic transceiver 130 may determine a transmission frequency of an ultrasonic signal to be transmitted and a reception bandwidth of an echo signal to be received based on information about a probe, and may transmit an ultrasonic signal according to the determined transmission frequency and receive an echo signal according to the determined reception bandwidth.

Operations of the first ultrasonic transceiver 130 will be described in detail later with reference to FIGS. 6 through 8.

The gel detector 135 may determine whether gel is applied on the probe 20 based on the echo signal received by the first ultrasonic transceiver 130. For example, when a value of the received echo signal is higher than a pre-set gel detection threshold value, the gel detector 135 may determine that gel is applied on the probe 20. However, an embodiment of the present invention is not limited thereto.

Here, a gel detection threshold value may be set based on an echo signal reflected in response to a transmitted ultrasonic signal, through a probe on which gel is applied. Also, the set gel detection threshold value may be stored in the memory 180.

The second ultrasonic transceiver 115 may transmit and receive ultrasonic signals to obtain an ultrasonic image, and may include a transmitter 110 and a receiver 120.

The transmitter 110 supplies a driving signal to the probe 20 and includes a pulse generator 112, a transmission delayer 114, and a pulser 116. The pulse generator 112 generates pulses for forming transmission ultrasonic signals based on a predetermined pulse repetition frequency (PRF), and the transmission delayer 114 applies a delay time to the pulses in order to determine transmission directionality of ultrasonic signal. Pulses to which a delay time is applied correspond to a plurality of vibrators included in the probe 20, respectively. The pulser 116 applies a driving signal (or a driving pulse) to the probe 20 at timing intervals corresponding to each pulse to which a delay time is applied.

The receiver 120 generates ultrasonic data by processing an echo signal received by the probe 20 and may include an amplifier 122, an analog-digital converter (ADC) 124, a reception delayer 126, and an adder 128. The amplifier 122 amplifies echo signals in each channel, and the ADC 124 analog-to-digital converts the amplified echo signals. The reception delayer 126 processes the digitally-converted echo signals by applying delay times for determining reception directionality to the digitally-converted echo signals, and the adder 128 generates ultrasonic data by adding the echo signals processed by the reception delayer 126.

The image processor 150 generates an ultrasonic image by scan-converting ultrasonic data generated by the second ultrasonic transceiver 115, and displays the ultrasonic image.

Meanwhile, an ultrasonic image may include not only a grayscale ultrasonic image obtained by scanning a target object in an A mode, a B mode, and a motion (M) mode, but also a Doppler image showing movement of the target object. Examples of the Doppler image include a blood flow Doppler image showing flow of blood (i.e., a color Doppler image), a tissue Doppler image showing movement of tissues, and a spectral Doppler image showing the speed at which a target object moves as a waveform.

A B mode processor 141 extracts B mode components from ultrasonic data and processes the B mode components. An image generator 155 may generate an ultrasonic image in which signal intensities are represented as brightness based on the extracted B mode components.

Similarly, a Doppler processor 142 may extract Doppler components from ultrasonic data, and the image generator 155 may generate a Doppler image indicating movement of a target object as colors or waveforms based on the extracted Doppler components.

The image generator 155 according to an embodiment of the present invention may generate a 2D ultrasonic image or may generate an elastic image in which deformation of the target object 10 according to pressure is visualized. Furthermore, the image generator 155 may display various types of additional information on an ultrasonic image by using text and graphics. Meanwhile, the generated ultrasonic image may be stored in the memory 180.

A display unit 160 displays the generated ultrasonic image. The display unit 160 may display not only an ultrasonic image, but also various types of information processed by the ultrasonic diagnostic apparatus 100 on a screen via a graphic user interface (GUI). Meanwhile, the ultrasonic diagnostic apparatus 100 may include two or more display units 160 according to embodiments of the present invention.

The display unit 160 may include at least one of a liquid crystal display, a thin film transistor-liquid crystal display, an organic light-emitting diode, a flexible display, a 3D display, and an electrophoretic display.

When the display unit 160 and a user input unit are combined in a layer structure to form a touch screen, the display unit 160 may also be used as an input device capable of receiving information according to a touch of a user, as well as an output device.

The touch screen may be configured to detect not only a touched area but also a pressure applied to the touched area. Also, the touch screen may be configured to detect not only a real-touch but also a proximity touch.

Herein, a 'real-touch' indicates a case where a pointer actually touches a screen, and a 'proximity-touch' indicates a case where a pointer does not actually touch a screen but approaches the screen while still maintaining a predetermined distance therefrom. Herein, a pointer is a touching tool for touching or proximity-touching a certain portion of a displayed screen. Examples of the pointer include an electronic pen or a finger.

Although not shown, the ultrasonic diagnostic apparatus 100 may include various sensors inside or near a touch screen to detect a real-touch or a proximity touch on the touch screen. An example of a sensor for detecting a touch on a touch screen includes a tactile sensor.

A tactile sensor is a sensor for detecting, with sensitivity similar to that of a person, contact of a certain target object. The tactile sensor may detect various types of information, for example, roughness of a contact surface, rigidness of the certain target object, and a temperature of a contact point.

Another example of the sensor for detecting a touch on a touch screen includes a proximity sensor. The proximity sensor is a sensor for detecting an existence of a target object approaching or near a predetermined detection surface by using force of an electromagnetic field or an infrared light, without having to detect a mechanical touch.

Examples of the proximity sensor include a transmission type photoelectric sensor, a direct reflection type photoelectric sensor, a mirror reflection type photoelectric sensor, a high frequency oscillation type proximity sensor, a capacitance type proximity sensor, a magnetic proximity sensor, and an infrared proximity sensor.

The communication unit 170 connected to a network 30 via wires or wirelessly and communicates with an external device or a server. The communication unit 170 may exchange data with a hospital server or another medical device in a hospital that is connected with a picture archiving and communications system (PACS). Furthermore, the communication unit 170 may perform data communication according to the digital imaging and communications in medicine (DICOM) standard.

The communication unit 170 may transmit and receive data related to diagnosis of a target object, e.g., an ultrasonic image, ultrasonic data, and Doppler data of the target object, via the network 30 and may also transmit and receive medical images obtained via other medical devices, e.g., a CT image, a MR image, and an X-ray image. Furthermore, the communication unit 170 may receive information related to a diagnosis history or treatment schedule of a patient from a server and utilize the information to diagnose the patient. Furthermore, the communication unit 170 may perform data communication not only with a server or a medical device in a hospital, but also with a portable terminal of a doctor or a patient.

The communication unit 170 is connected to the network 30 via wires or wirelessly and may exchange data with a server 32, a medical device 34, or a portable terminal 36. The communication unit 170 may include one or more components that enable communication with external devices, e.g., a close-distance communication module 171, a wired communication module 172, and a mobile communication module 173.

The close-distance communication module 171 may refer to a module for close-distance communication within a predetermined distance. Examples of close-distance communication techniques according to an embodiment of the present invention may include wireless LAN, Wi-Fi, Bluetooth, Zigbee, Wi-Fi Direct (WFD), ultra wideband (UWB), infrared data association (IrDA), Bluetooth Low Energy (BLE), and near field communication (NFC), but are not limited thereto.

The wired communication module 172 refers to a module for communication using electric signals or optical signals. Examples of wired communication techniques according to an embodiment of the present invention may include a pair cable, a coaxial cable, an optical fiber cable, and an Ethernet cable.

The mobile communication module 173 transmits and receives wireless signals with at least one from among a station, an external terminal, and a server on a mobile communication network. Here, the wireless signals may include voice call signals, video call signals, or various types of data for transmission and reception of text/multimedia messages.

The memory 180 stores various types of data processed by the ultrasonic diagnostic apparatus 100. For example, the memory 180 may store medical data related to diagnosis of a target object, such as ultrasonic data and ultrasonic image that are input or output, and may also store algorithms or programs to be executed in the ultrasonic diagnostic apparatus 100.

According to an embodiment of the present invention, the memory 180 may pre-map and store a cross section information image corresponding to cross section information of a target object. For example, the memory 180 may store a first cross section information image corresponding to first cross section information, and a second cross section information image corresponding to second cross section information. Cross section information may include various types of data for identifying cross sections of a target object. For example, the first cross section information may include data about a shape, a length, or an area of an object included only in an ultrasonic image of a first cross section of a target object, or may include a brightness value of a certain range only shown in the first cross section image.

The memory 180 may be embodied as any of various storage media, e.g., a flash memory, a hard disk drive, an EEPROM, etc. Furthermore, the ultrasonic diagnostic apparatus 100 may utilize a web storage server or a cloud server that functions as the memory 180 online.

The user input unit 190 generates input data that is input by the user to control operations of the ultrasonic diagnostic apparatus 100. The user input unit 190 may include hardware components, such as a keypad, a mouse, a touch pad, a track ball, and a jog switch, but alternatively, the user input unit 190 may further include various components, such as an electrocardiogram measuring module, a respiration measuring module, a voice recognition sensor, a gesture recognition sensor, a fingerprint recognition sensor, an iris recognition sensor, a depth sensor, a distance sensor, etc.

According to an embodiment of the present invention, the user input unit 190 may receive a user input for selecting any one of a first ultrasonic image and a second ultrasonic image, or may receive a user input for selecting any one of a plurality of cross sections included in a cross section information image.

In detail, a touch pad may include a touch screen that has a layer structure including the display unit 160 described above.

Here, the ultrasonic diagnostic apparatus 100 according to an embodiment of the present invention may display an ultrasonic image in a predetermined mode and a control panel for the ultrasonic image on a touch screen. Also, the ultrasonic diagnostic apparatus 100 may detect a touch gesture of a user on the ultrasonic image through the touch screen.

The ultrasonic diagnostic apparatus 100 according to an embodiment of the present invention may physically provide, in a control panel of a general ultrasonic apparatus, buttons which are frequently used by a user, while providing remaining buttons via a touch screen in forms of a GUI.

The controller 195 may control overall operations of the ultrasonic diagnostic apparatus 100. In other words, the controller 195 may control operations among the probe 20, the first and second ultrasonic transceivers 130 and 115, the image processor 150, the communication unit 170, the memory 180, and the user input unit 190 of FIG. 2.

All or some of the probe 20, the second ultrasonic transceiver 115, the image processor 150, the communication unit 170, the memory 180, the user input unit 190, and the controller 195 may be implemented as software modules. However, an embodiment of the present invention is not limited thereto, and some of the components stated above may be implemented as hardware modules. Furthermore, at least one of the second ultrasonic transceiver 115, the image processor 150, and the communication unit 170 may be included in the controller 195. However, an embodiment of the present invention is not limited thereto.

Figure 3:
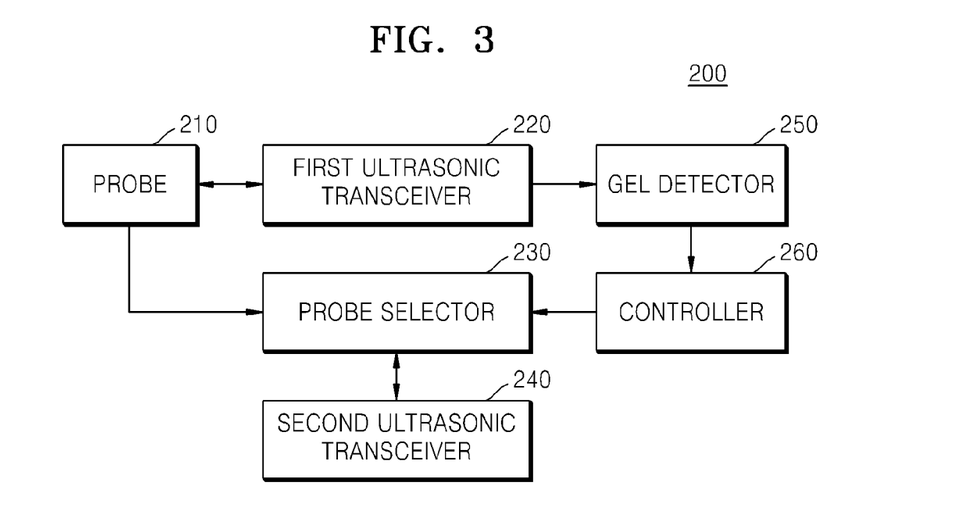
FIG. 3 is a block diagram of an ultrasonic diagnostic apparatus according to another embodiment of the present invention.
Figure 4:
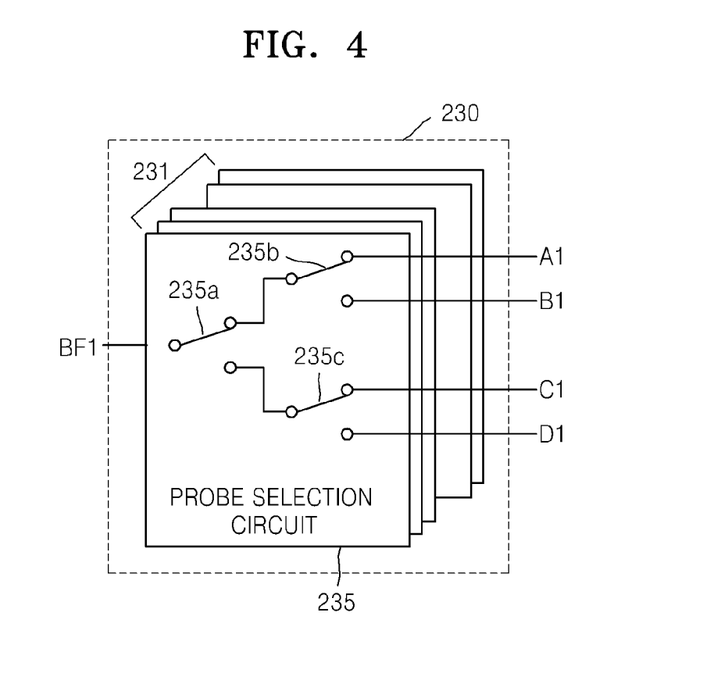
FIG. 4 is a diagram for describing a probe selector of FIG. 3.
Figure 5:
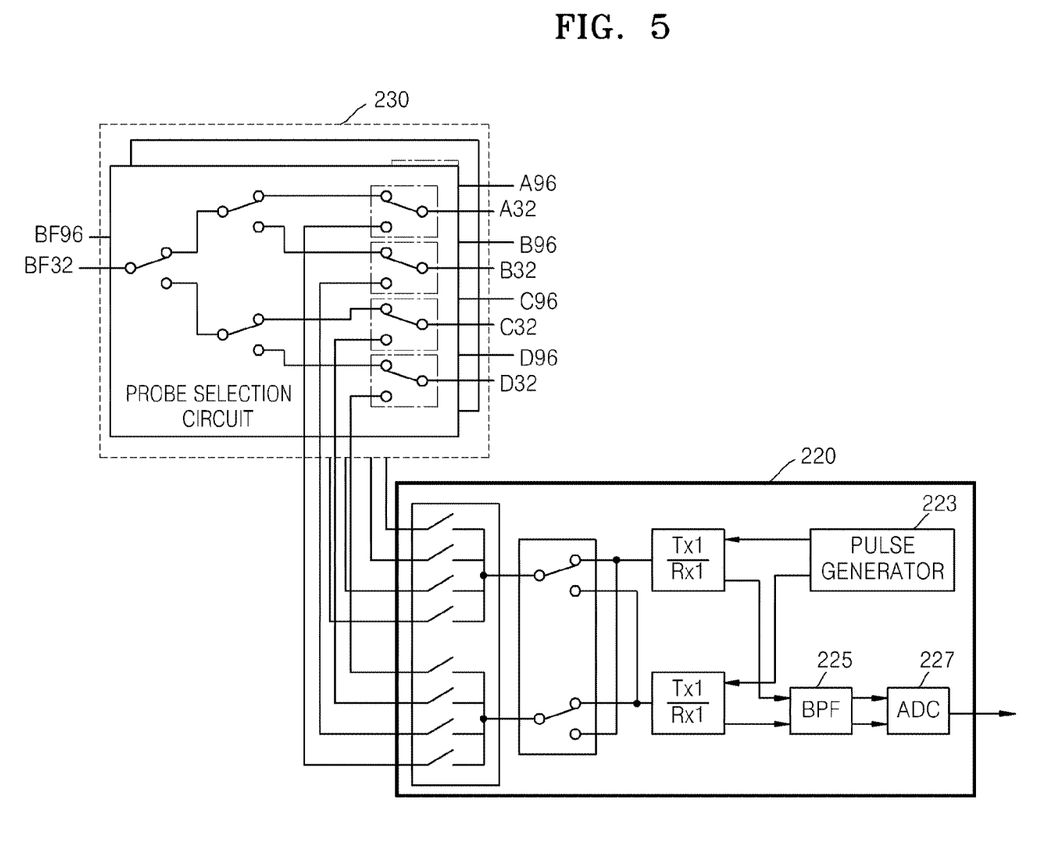
FIG. 5 is a diagram for describing a first ultrasonic transceiver of FIG. 3.

FIG. 3 is a block diagram of an ultrasonic diagnostic apparatus 200 according to another embodiment of the present invention, FIG. 4 is a diagram for describing a probe selector 230 of FIG. 3, and FIG. 5 is a diagram for describing a first ultrasonic transceiver 220 of FIG. 3.

Referring to FIG. 3, the ultrasonic diagnostic apparatus 200 may include a probe 210, the probe selector 230, the first ultrasonic transceiver 220, a second ultrasonic transceiver 240, a gel detector 250, and a controller 260.

The probe 210 of FIG. 3 corresponds to the probe 20 of FIG. 2, and may include a plurality of transducer elements. Each transducer element may transmit an ultrasonic signal to a target object according to a driving signal applied from the first or second ultrasonic transceiver 220 or 240, and may receive an echo signal reflected from the target object.

The probe selector 230 may activate at least one of a plurality of the probes 210 respectively connected to probe ports. In order to obtain an ultrasonic image, an activated probe may transmit an ultrasonic signal to a target object according to a driving signal applied from the second ultrasonic transceiver 240, and receive an echo signal reflected from the target object.

For example, the second ultrasonic transceiver 240 of FIG. 3 may include a beam former, and a probe activated by the probe selector 230 may be electrically connected to the beam former. Here, the beam former may include the transmitter 110 and the receiver 120 of FIG. 2.

Referring to FIG. 4, the probe selector 230 may include a plurality of probe selection circuits for connecting the beam former and the probe port. For example, when the probe 210 includes 128 transducer elements, the second ultrasonic transceiver 240 includes 128 beam forming circuits, and 128 channels are formed, the probe selector 230 may include 128 probe selection circuits 231, i.e., first through 128th probe selection circuits.

Hereinafter, for convenience of description, one or more embodiments of the present invention will be described based on a first probe selection circuit 235 that is one of the 128 probe selection circuits 231. Accordingly, descriptions about the first probe selection circuit 235 may also be applied to the second through 128th probe selection circuits.

As shown in FIG. 4, the first probe selection circuit 235 may include a mechanical or electronic switch (hereinafter, referred to as a switch), and for example, when the number of probe ports is 4, the first probe selection circuit 235 may include three switches 235a through 235c, but an embodiment of the present invention is not limited thereto.

For example, when a probe port A in FIG. 1 is to be connected to a beam former BF, the first probe selection circuit 235 may use the two switches 235a and 235b to electrically connect a probe port A1 corresponding to the first channel to a beam former BF1. Similarly to the first probe selection circuit 235, the second through 128th probe selection circuits may electrically connect probe ports A2 through A128 corresponding to second through 128th channels to beam formers BF2 through BF128, respectively.

Accordingly, the second ultrasonic transceiver 240 may process an echo signal received through the activated probe.

In order to determine whether gel is applied on a probe connected to a probe port, the first ultrasonic transceiver 220 may apply a driving signal to the probe and receive an echo signal. For example, referring to FIG. 5, the first ultrasonic transceiver 220 may include circuits connected to a plurality of probe ports, and the first ultrasonic transceiver 220 may use a plurality of switches to electrically connect probe ports corresponding to certain elements (in FIG. 5, 32nd and 96th elements included in a plurality of probes to pulse transmitter Tx1 and Tx2 or receivers Rx1 and Rx2. Here, the certain elements may be changed according to probes or to improve functions.

Also, the first ultrasonic transceiver 220 includes a pulse generator 223, and the pulse generator 223 may generate a pulse having a frequency in a physically transmittable band in a probe based on probe information, and transmit the generated pulse to the pulse transmitters Tx1 and Tx2.

Also, the first ultrasonic transceiver 220 may include a band pass filter (BPF) 225, and may input a signal having a bandwidth through which the frequency in the transmittable band may pass, from among signals received by the receivers Rx1 and Rx2, to an ADC 227.

The echo signal that is processed may be input to the gel detector 250, and the gel detector 250 may determine whether gel is applied on a probe based on a value of the echo signal.

The gel detector 250 may compare the value of the echo signal and a pre-set gel detection threshold value, and determine that the gel is applied on the probe when the value of the echo signal is higher than the pre-set gel detection threshold value. Setting of a gel detection threshold value will be described in detail later with reference to FIGS. 6 and 7.

When it is determined that the gel is applied on the probe, the controller 260 may activate the probe. For example, the controller 260 may transmit a probe change command to the probe selector 230 to deactivate a currently activated probe and activate the probe on which the gel is applied.

Meanwhile, the ultrasonic diagnostic apparatuses 100 and 200 of FIGS. 2 and 3 are only examples, and components of the ultrasonic diagnostic apparatuses 100 and 200 may be combined or omitted, or a new component may be added based on specifications of an actual ultrasonic diagnostic apparatus. In other words, two or more components may be combined into one component or one component may be divided into two or more components if required. Also, functions performed by each component are for describing one or more embodiments of the present invention, and detailed operations or apparatuses do not limit the scope of the invention.

Figure 6:
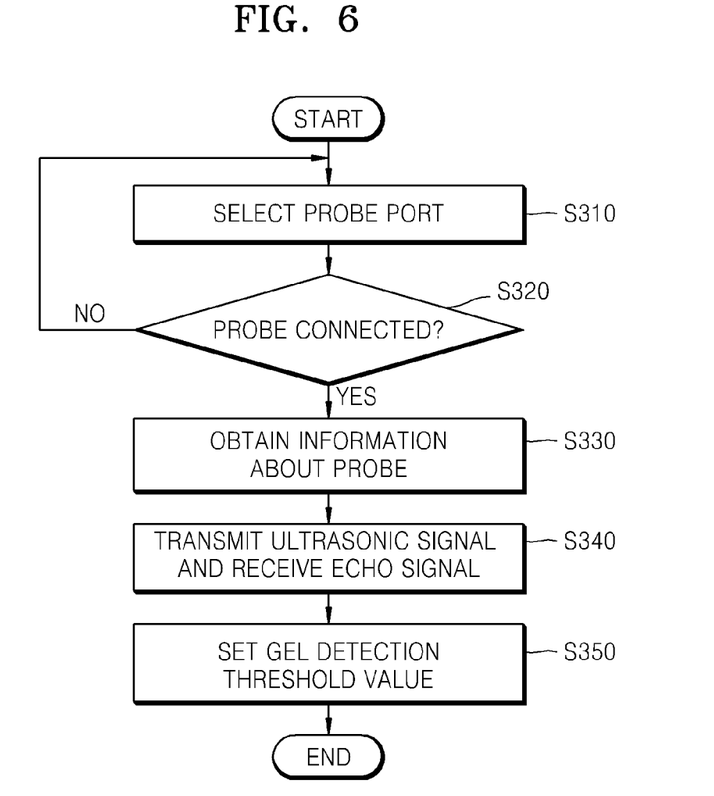
FIG. 6 is a flowchart of a method of operating an ultrasonic diagnostic apparatus, according to an embodiment of the present invention.
Figure 7A:
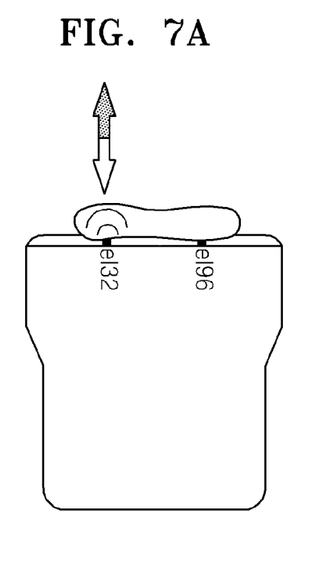
Figure 7B:
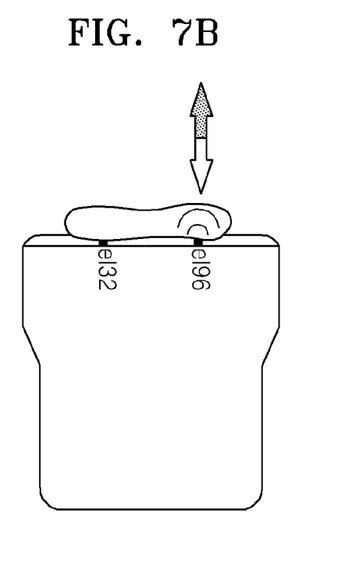
Figure 7C:
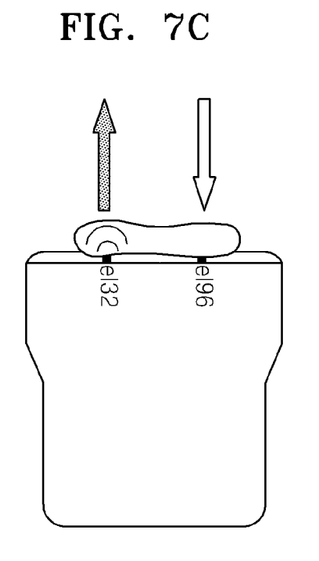
Figure 7D:
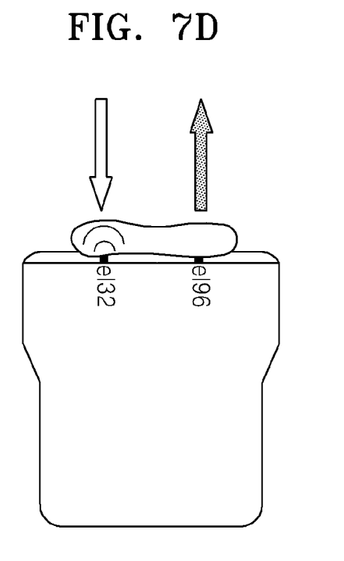

FIG. 6 is a flowchart of a method of operating the ultrasonic diagnostic apparatus 100 or 200, according to an embodiment of the present invention, and FIG. 7 illustrates reference diagrams for describing the method of FIG. 6.

Referring to FIG. 6, the ultrasonic diagnostic apparatus 100 or 200 selects a probe port in operation S310, and may determine whether a probe is connected to the selected probe port in operation S320. For example, as shown in FIG. 1, when the ultrasonic diagnostic apparatus 100 includes four probe ports A through D, it may be determined whether a probe is connected to the probe ports A through D.

When it is determined that the probe is connected to the selected probe port, the ultrasonic diagnostic apparatus 100 or 200 may obtain information about the connected probe in operation S330.

For example, an identification (ID) of the probe connected to the probe port may be recognized and then compared to a pre-stored ID of the probe, and corresponding information about the probe may be obtained.

Also, the ultrasonic diagnostic apparatus 100 or 200 may transmit an ultrasonic signal and receive an echo signal through a probe on which gel is applied based on the obtained information, in operation S340.

Here, the ultrasonic diagnostic apparatus 100 or 200 may transmit an ultrasonic signal having a transmission frequency that is physically transmittable from the probe, and receive an echo signal having a reception bandwidth corresponding to the transmission frequency, based on the information. Also, the ultrasonic diagnostic apparatus 100 or 200 may transmit an ultrasonic signal and receive an echo signal through at least one element included in the probe. Here, the ultrasonic diagnostic apparatus 100 or 200 may transmit an ultrasonic signal and receive an echo signal through first and second elements included in the probe.

For example, referring to FIG. 7, when the probe has 128 elements, the first element may be a 32nd element el32, and the second element may be a 96th element el96. However, an embodiment of the present invention is not limited thereto, and any number of elements may be selected in any method.

As shown in FIG. 7 (*a*), the ultrasonic diagnostic apparatus 100 or 200 may transmit an ultrasonic signal through the first element (32nd element el32) and receive an echo signal through the first element (32nd element el32) in a first mode.

Alternatively, as shown in FIG. 7 (*b*), the ultrasonic diagnostic apparatus 100 or 200 may transmit an ultrasonic signal through the second element (96th element el96) and receive an echo signal through the second element (96th element el96) in a second mode.

Alternatively, as shown in FIG. 7 (*c*), the ultrasonic diagnostic apparatus 100 or 200 may transmit an ultrasonic signal through the first element (32nd element el32) and receive an echo signal through the second element (96th element el96) in a third mode.

Alternatively, as shown in FIG. 7 (*d*), the ultrasonic diagnostic apparatus 100 or 200 may transmit an ultrasonic signal through the second element (96th element el96) and receive an echo signal through the first element (32nd element el32) in a fourth mode.

However, operations of the first ultrasonic transceiver 220 are not limited to the first through fourth modes described above, and the first ultrasonic transceiver 220 may transmit an ultrasonic signal and receive an echo signal in any operation mode based on the number of elements for transmitting an ultrasonic signal and receiving an echo signal.

Meanwhile, the first ultrasonic transceiver 220 may set a gel detection threshold value based on the received echo signal in operation S350.

For example, when the first ultrasonic transceiver 220 receives echo signals by operating in the first through fourth modes described above with reference to FIG. 7, the first ultrasonic transceiver 220 may set first through fourth gel detection threshold values based on the echo signals received in the first through fourth modes. Also, the first through fourth gel detection threshold values may be stored in the memory 180.

Meanwhile, a gel detection threshold value may be set by performing operations S330 through S350 on another probe connected to another probe port.

When power is supplied to the ultrasonic diagnostic apparatus 100 or 200, operations S310 through S350 of FIG. 6 are performed, and then operations S310 through S350 of FIG. 6 may be performed whenever a connected probe is changed by monitoring whether a new probe is connected to a probe port.

Figure 8:
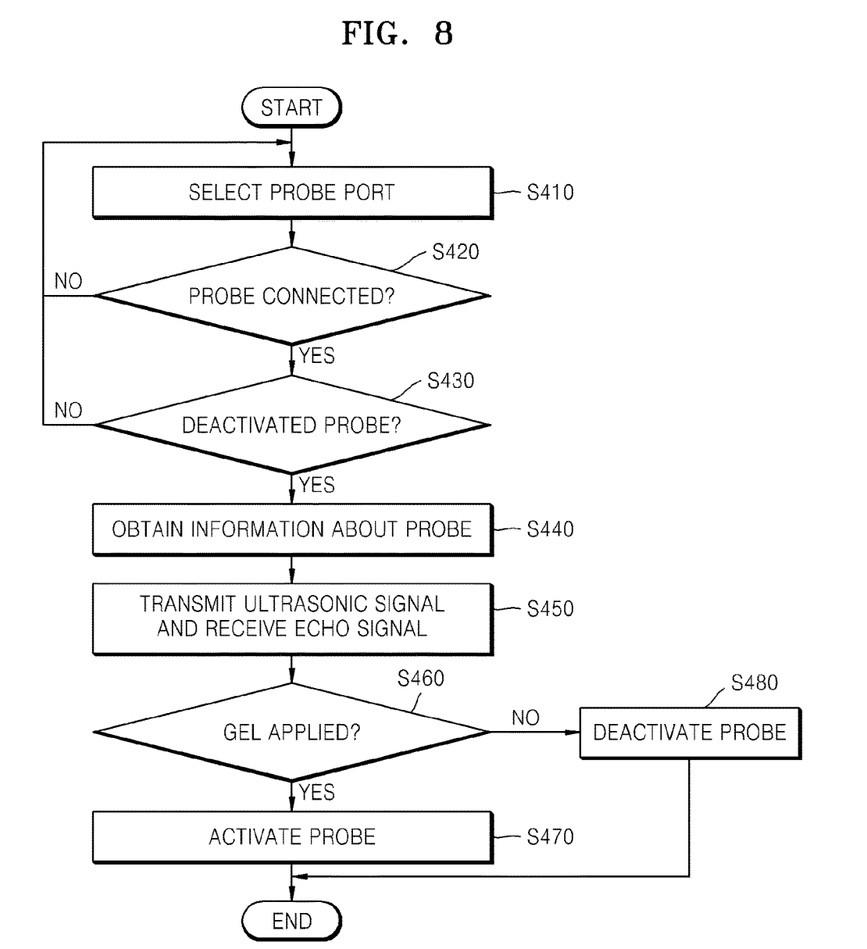
FIG. 8 is a flowchart of a method of operating an ultrasonic diagnostic apparatus, according to another embodiment of the present invention.

FIG. 8 is a flowchart of a method of operating the ultrasonic diagnostic apparatus 100 or 200, according to another embodiment of the present invention.

Referring to FIG. 8, the ultrasonic diagnostic apparatus 100 or 200 may select any one of a plurality of probe ports in operation S410 and determine whether a probe is connected to the selected probe port in operation S420.

Here, when a probe is not connected, the ultrasonic diagnostic apparatus 100 or 200 may select another probe port to determine whether a probe is connected to the other probe port.

On the other hand, when a probe is already connected to a probe port, the ultrasonic diagnostic apparatus 100 or 200 may determine whether the connected probe is a deactivated probe in operation S430. For example, the ultrasonic diagnostic apparatus 100 or 200 may check a connection state between the probe port to which a probe is connected and the second ultrasonic transceiver 115 or 240 to determine whether the probe is a deactivated probe.

When the probe is an activated probe, the ultrasonic diagnostic apparatus 100 or 200 may select another probe port to perform operations S420 and S430.

On the other hand, when the probe is a deactivated probe, the ultrasonic diagnostic apparatus 100 or 200 may obtain information about the deactivated probe in operation S440.

For example, an ID of the probe connected to the probe port may be recognized and then compared with a pre-stored ID of the probe, and corresponding information about the probe may be obtained.

Also, the ultrasonic diagnostic apparatus 100 or 200 may transmit an ultrasonic signal and receive an echo signal in operation S450 through the deactivated probe, based on the obtained information.

Here, the ultrasonic diagnostic apparatus 100 or 200 may transmit an ultrasonic signal having a transmission frequency that is physically transmittable from the probe, and receive an echo signal having a reception bandwidth corresponding to the transmission frequency, based on the information about the probe.

Also, the ultrasonic diagnostic apparatus 100 or 200 may transmit an ultrasonic signal and receive an echo signal through at least one element included in the probe. Here, the ultrasonic diagnostic apparatus 100 or 200 may transmit an ultrasonic signal and receive an echo signal through first and second elements included in the probe, and for example, as described above with reference to FIG. 7, may transmit an ultrasonic signal and receive an echo signal in one of the first through fourth modes.

Accordingly, the ultrasonic diagnostic apparatus 100 or 200 may receive a first echo signal in the first mode, a second echo signal in the second mode, a third echo signal in the third mode, and a fourth echo signal in the fourth mode, and may obtain values of the first through fourth echo signals.

Also, the ultrasonic diagnostic apparatus 100 or 200 may determine whether gel is applied on the deactivated probe in operation S460 by comparing a gel detection threshold value that is pre-set according to the method described above with reference to FIG. 6, and the value of the echo signal obtained in operation S450.

For example, the ultrasonic diagnostic apparatus 100 or 200 may determine that the gel is applied on the probe when the value of the echo signal is higher than the gel detection threshold value. Alternatively, the ultrasonic diagnostic apparatus 100 or 200 may determine whether the gel is applied on the probe by comparing the values of the first through fourth echo signals respectively with first through fourth gel detection threshold values.

When it is determined that the gel is applied on the probe, the ultrasonic diagnostic apparatus 100 or 200 may activate the probe in operation S470.

For example, a probe change command may be transmitted to the probe selector 230 to deactivate a currently activated probe and activate the probe on which the gel is applied.

On the other hand, when it is determined that the gel is not applied on the probe, the ultrasonic diagnostic apparatus 100 or 200 may maintain the probe to be in a deactivated state in operation S480.

As described above, according to the one or more of the above embodiments of the present invention, a process of changing a probe may be removed or reduced by manipulating a control panel of an ultrasonic diagnostic apparatus, thereby increasing convenience of using the ultrasonic diagnostic apparatus and reducing an ultrasonic diagnosis time.

Also, a user may be less stressed by preventing repeated operations of changing a probe by manipulating the control panel.

The invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, etc. The computer readable recording medium can also be distributed over network coupled computer systems so that the computer readable code is stored and executed in a distributed fashion.

While this invention has been particularly shown and described with reference to embodiments thereof, it will be understood by those of ordinary skill in the art that various changes in form and details may be made therein without departing from the spirit and scope of the invention as defined by the appended claims. The embodiments should be considered in a descriptive sense only and not for purposes of limitation. Therefore, the scope of the invention is defined not by the detailed description of the invention but by the appended claims, and all differences within the scope will be construed as being included in the present invention.

What is claimed is:

1. An ultrasonic diagnostic apparatus comprising:
a first ultrasonic transceiver that transmits an ultrasonic signal by applying a first driving signal to a deactivated probe from among a plurality of probes connected to probe ports of the ultrasonic diagnostic apparatus, and receives a first echo signal that is reflected, through the deactivated probe; and
a controller that determines whether gel is applied on the deactivated probe based on the first echo signal and activates the deactivated probe when the gel is applied on the deactivated probe by electrically connecting the deactivated probe to a beam former in a second ultrasonic transceiver of the ultrasonic diagnostic apparatus,
wherein the second ultrasonic transceiver transmits an ultrasonic signal to an object by applying a second driving signal to the activated probe from among the plurality of probes, and receives a second echo signal that is reflected from the object, through the activated probe, and
wherein the controller generates an ultrasonic image representing the object based on the second echo signal.

2. The ultrasonic diagnostic apparatus of claim 1, wherein the controller obtains a transmission frequency and a reception bandwidth corresponding to the deactivated probe, based on identification information of the deactivated probe, and
the first ultrasonic transceiver transmits the ultrasonic signal according to the transmission frequency, and receives the first echo signal according to the reception bandwidth.

3. The ultrasonic diagnostic apparatus of claim 1, wherein the first ultrasonic transceiver transmits the ultrasonic signal and receives the first echo signal by applying the driving signal to one or two transducer elements from among a plurality of transducer elements of the deactivated probe.

4. The ultrasonic diagnostic apparatus of claim 1, wherein the deactivated probe comprises a first transducer element and a second transducer element, and
the first ultrasonic transceiver operates in at least one of a first mode for transmitting the ultrasonic signal and receiving the first echo signal through the first transducer element, a second mode for transmitting the ultrasonic signal and receiving the first echo signal through the second transducer element, a third mode for transmitting the ultrasonic signal through the first transducer element and receiving the first echo signal through the second transducer element, and a fourth mode for transmitting the ultrasonic signal through the second transducer element and receiving the first echo signal through the first transducer element.

5. The ultrasonic diagnostic apparatus of claim 1, wherein the controller determines that the gel is applied on the deactivated probe when a value of the first echo signal is higher than a gel detection threshold value.

6. The ultrasonic diagnostic apparatus of claim 1,
wherein the controller deactivates a preactivated probe from among the plurality of probes by electrically disconnecting the preactivated probe from the beam former in the second ultrasonic transceiver.

7. The ultrasonic diagnostic apparatus of claim 1, wherein the controller determines a probe from among the plurality of probes as the deactivated probe based on whether the probe is connected to the beam former in the second ultrasonic transceiver.

8. A method of operating an ultrasonic diagnostic apparatus, the method comprising:

causing a first ultrasonic transceiver to transmit an ultrasonic signal by applying a first driving signal to a deactivated probe from among a plurality of probes connected to probe ports of the ultrasonic diagnostic apparatus, and receive a first echo signal that is reflected, through the deactivated probe;

determining whether gel is applied on the deactivated probe based on the received first echo signal;

activating the deactivated probe when the gel is applied on the deactivated probe by electrically connecting the deactivated probe to a beam former in a second ultrasonic transceiver of the ultrasonic diagnostic apparatus;

causing the second ultrasonic transceiver to transmit an ultrasonic signal to an object by applying a second driving signal to the activated probe, and receive a second echo signal that is reflected from the object, through the activated probe; and generating an ultrasonic image representing the object based on the second echo signal.

9. The method of claim 8, further comprising obtaining a transmission frequency and a reception bandwidth corresponding to the deactivated probe, based on identification information of the deactivated probe, wherein the causing the first ultrasonic transceiver to transmit of the ultrasonic signal and receive the first echo signal comprises causing the first ultrasonic transceiver to transmit the ultrasonic signal according to the transmission frequency, and receive the first echo signal according to the reception bandwidth.

10. The method of claim 8, wherein the causing the first ultrasonic transceiver to transmit of the ultrasonic signal and receive the first echo signal comprises causing the first ultrasonic transceiver to transmit the ultrasonic signal and receive the first echo signal by applying the driving signal to one or two transducer element form among a plurality of transducer elements of the deactivated probe.

11. The method of claim 8, wherein the deactivated probe comprises a first transducer element and a second transducer element, and the causing the first ultrasonic transceiver to transmit the ultrasonic signal and receive the first echo signal comprises at least one of operating in a first mode for transmitting the ultrasonic signal and receiving the first echo signal through the first transducer element, operating in a second mode for transmitting the ultrasonic signal and receiving the first echo signal through the second transducer element, operating in a third mode for transmitting the ultrasonic signal through the first transducer element and receiving the first echo signal through the second transducer element, and operating in a fourth mode for transmitting the ultrasonic signal through the second transducer element and receiving the first echo signal through the first transducer element.

12. The method of claim 8, wherein the determining of whether the gel is applied on the deactivated probe comprises determining that the gel is applied on the deactivated probe when a value of the first echo signal is higher than a gel detection threshold value.

13. The method of claim 8, further comprising:

deactivating a preactivated probe from among the plurality of probes by electrically disconnecting the preactivated probe from the beam former in the second ultrasonic transceiver.

14. The method of claim 8, further comprising determining a probe from among the plurality of probes as the deactivated probe based on whether the probe is connected to the beam former in the second ultrasonic transceiver.

15. A non-transitory computer-readable recording medium having recorded thereon a program for executing a method of operating an ultrasonic diagnostic apparatus, that when executed by a processor, performs the method comprising:

causing a first ultrasonic transceiver to transmit an ultrasonic signal by applying a first driving signal to a deactivated probe from among a plurality of probes connected to probe ports of the ultrasonic diagnostic apparatus, and receive a first echo signal that is reflected, through the deactivated probe;

determining whether gel is applied on the deactivated probe based on the received first echo signal;

activating the deactivated probe when the gel is applied on the deactivated probe by electrically connecting the deactivated probe to a beam former in a second ultrasonic transceiver of the ultrasonic diagnostic apparatus;

causing the second ultrasonic transceiver to transmit an ultrasonic signal to an object by applying a second driving signal to the activated probe, and receive a second echo signal that is reflected from the object, through the activated probe; and generating an ultrasonic image representing the object based on the second echo signal.

* * * * *